(12) United States Patent
Hannus et al.

(10) Patent No.: US 10,375,963 B2
(45) Date of Patent: Aug. 13, 2019

(54) **ALKALI METAL SALT FOR USE IN TREATMENT OF *VARROA DESTRUCTOR* MITE INFESTATION OF HONEY BEES**

(71) Applicants: Universität Hohenheim, Stuttgart (DE); Stefan Hannus, Munich (DE); siTools Biotech GmbH, Martinsried (DE)

(72) Inventors: Stefan Hannus, Munich (DE); Peter Rosenkranz, Tübingen (DE); Bettina Ziegelmann, Stuttgart (DE)

(*) Notice: Subject to any disclaimer, the term of this patent is extended or adjusted under 35 U.S.C. 154(b) by 0 days.

(21) Appl. No.: 15/758,283

(22) PCT Filed: Sep. 7, 2016

(86) PCT No.: PCT/EP2016/071124
§ 371 (c)(1),
(2) Date: Mar. 7, 2018

(87) PCT Pub. No.: WO2017/042240
PCT Pub. Date: Mar. 16, 2017

(65) Prior Publication Data
US 2018/0255783 A1    Sep. 13, 2018

(30) Foreign Application Priority Data
Sep. 9, 2015  (GB) .................................. 1515960.1

(51) Int. Cl.
*A01N 59/08*  (2006.01)
*A01N 59/00*  (2006.01)
*A01N 37/02*  (2006.01)
*A01N 37/36*  (2006.01)
*A01N 59/02*  (2006.01)

(52) U.S. Cl.
CPC ............ *A01N 59/08* (2013.01); *A01N 37/02* (2013.01); *A01N 37/36* (2013.01); *A01N 59/00* (2013.01); *A01N 59/02* (2013.01)

(58) Field of Classification Search
CPC ........ A01N 59/08; A01N 59/00; A01N 37/02; A01N 37/36; A01N 59/02
See application file for complete search history.

(56) References Cited

U.S. PATENT DOCUMENTS

2011/0171324 A1   7/2011  Clemente

FOREIGN PATENT DOCUMENTS

| WO | WO 2007/120461 A2 | 10/2007 | |
| WO | WO-2007120461 A2 * | 10/2007 | ............. A01K 51/00 |
| WO | WO 2011/045796 A1 | 4/2011 | |
| WO | WO 2012/170420 A2 | 12/2012 | |
| WO | WO-2012170420 A2 * | 12/2012 | ............. A01K 51/00 |
| WO | WO 2013/160393 A1 | 10/2013 | |
| WO | WO 2014/107664 A1 | 7/2014 | |
| WO | WO-2014107664 A1 * | 7/2014 | ............. A01N 65/08 |

OTHER PUBLICATIONS

Victoria Hurst, Philip C. Stevenson, Geraldine A. Wright, Toxins Induce 'Malaise' Behavior in the Honeybee (*Apis mellifera*), 200 J Comp. Physiol. A, 881 (Year: 2014).*
"A Database of *Drosophila* Genes & Genomes," FlyBase, http://flybase.org, accessed on Aug. 6, 2018.
"Online Gene Essentiality," OGEE, http://ogeedb.embl.de, accessed on Aug. 6, 2018.
Cornman, S. R., et al., "Genomic survey of the ectoparasitic mite *Varroa destructor*, a major pest of the honey bee *Apis mellifera*," *BMC Genomics*, vol. 11(602): 1-15 (2010).
Garbian, Y., et al., "Bidirectional Transfer of RNAi between Honey Bee and *Varroa destructor*: *Varroa* Gene Silencing Reduces *Varroa* Population," *PLOS: Pathogens*, vol. 8(12): 1-9 (2012).
Hurst, V., et al., "Toxins induce 'malaise' behaviour in the honeybee (*Apis mellifera*)," *J Comp Physiol A*, vol. 200(10): 881-890 (2014).

* cited by examiner

*Primary Examiner* — Sean M Basquill
(74) *Attorney, Agent, or Firm* — Sterne, Kessler, Goldstein & Fox P.L.L.C.

(57) ABSTRACT

The present disclosure relates to the use of alkali metal salts and preferably lithium chloride for treatment of *Varroa destructor* infestation of honey bees.

15 Claims, 6 Drawing Sheets

Figure 1:
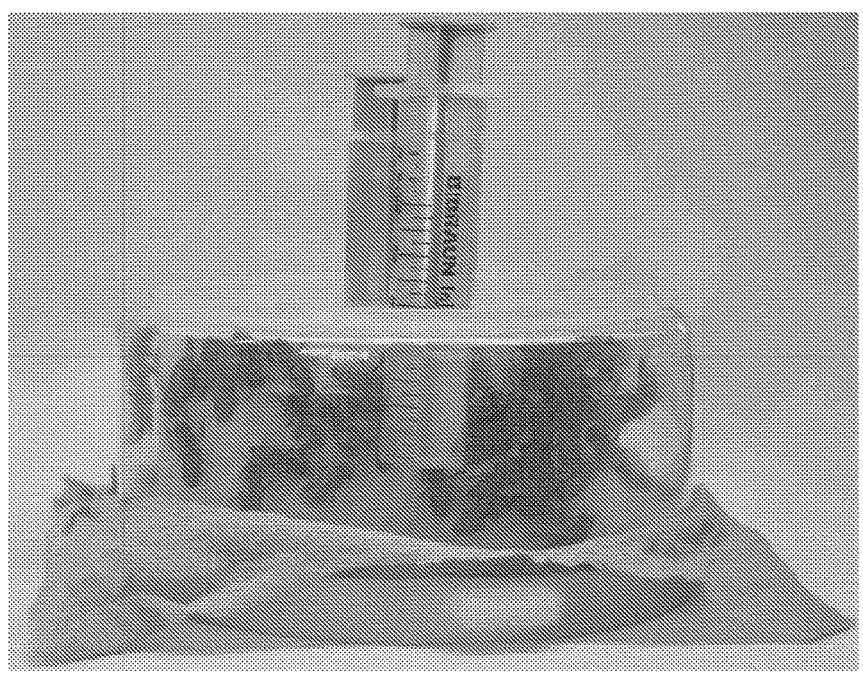

ALKALI METAL SALT FOR USE IN TREATMENT OF *VARROA DESTRUCTOR* MITE INFESTATION OF HONEY BEES

FIELD OF THE INVENTION

The present invention relates to the prophylactic and/or therapeutic treatment of *Varroa destructor* infestation of bees by using alkali metal salt, lithium salt and in particular LiCl.

BACKGROUND OF THE INVENTION

The honey bee, *Apis mellifera*, is the third most important animal for agricultural production following swine and cattle. Honey bees required for effective pollination of crops are therefore critical to world agriculture. Industrial production of fruits, vegetables and oleiferous fruits is in particular dependent on honey bees. Against this background the massive collapse of honeybee colonies is threatening worldwide agriculture, in particular in the US and Europe.

The honey bee health is threatened by many factors such as diseases, pesticides or malnutrition in areas of monoculture. Among all the factors affecting the bees, the ectoparasitic mite *Varroa destructor* is considered to be the main threat to bee health *Varroa destructor* is an external parasitic mite that attacks the honey bees *Apis cerana* and *Apis mellifera*. The disease caused by the mites is called varroosis. *Varroa* mites parasitize pupae and adult bees and reproduce in the pupal brood cells. The mites use specialized mouthparts to puncture the cuticle and feed on the bees' hemolymph which weakens the bees. The injured bees are also more prone to infections. *Varroa* mites are moreover assumed to be vectors for a number of honey bee pathogens, including deformed wing virus (DWV), Kashmir bee virus (KBV), acute bee paralysis virus (ABPV) and black queen cell virus (BQCV).

A significant mite infestation will lead to the death of a honey bee colony, usually in late summer or during overwintering. The *Varroa* mite is the parasite with the most pronounced economic impact on the beekeeping industry and may be one of the core factors for honey bee colony losses including CCD.

*Varroa* mites have been treated chemically with commercially available miticides, synthetic chemicals such as Fluvalinate and Coumaphos, or naturally occurring chemicals such as formic acid, oxalic acids, lactic acid, mineral oils and others. Non-chemical treatment approaches include the so-called perforated bottom board method, drone brood removal, heat treatments, comb trapping method and others. Recently RNA interference to knock down genes in the *Varroa* mite have been advocated, see for example WO 2011/045796.

There is nevertheless a continuing need for other treatment options against infestation of colonies of honeybees with *Varroa destructor*.

OBJECTIVES AND SUMMARY OF THE INVENTION

It is one objective of the present disclosure to provide compounds and compositions which can be used to prophylactically and/or therapeutically treat *Varroa destructor* infestations of bees, in particular of *Apis mellifera* honeybees.

It is another objective of the present disclosure to provide methods which can be used to prophylactically and/or therapeutically treat *Varroa destructor* infestations of bees, in particular of *Apis mellifera* honeybees.

These and other objectives as they may become apparent from the ensuing disclosure can be attained by the subject matter of the independent claims. Some of the specific embodiments considered by the present disclosure form the subject matter of the dependent claims.

The present disclosure as illustratively described in the following may suitably be practiced in the absence of any element or elements, limitation or limitations, not specifically disclosed herein.

The present disclosure will be described with respect to particular aspects and embodiments thereof and with reference to certain figures and examples but the invention is not limited thereto but only by the claims.

Technical terms are used by their common sense unless indicated otherwise. If a specific meaning is conveyed to certain terms, definitions of terms will be given in the following in the context of which the terms are used.

Where the term "comprising" is used in the present description and claims, it does not exclude other elements. For the purposes of the present disclosure, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present disclosure, the term "obtained" is considered to be a preferred embodiment of the term "obtainable".

Where an indefinite or definite article is used when referring to a singular noun, e.g. "a", "an" or "the", this includes a plural of that noun unless something else is specifically stated.

The terms "about" or "approximately" denote an interval of accuracy that the person skilled in the art will understand to still ensure the technical effect of the feature in question. The term typically indicates deviation from the indicated numerical value of ±10%, and preferably of ±5%.

As used herein, the terms "treatment", "treating" and the like, refer to obtaining a desired pharmacologic and/or physiologic effect. The effect may be prophylactic in terms of completely or partially preventing a disease or symptom thereof from developing and/or may be therapeutic in terms of a partial or complete reduction for an already established or developing disease or condition and/or adverse effect(s) attributable to an already established or developing disease or condition.

Prophylactic treatment thus includes preventing the disease or condition and/or adverse events associated with the disease or condition from occurring in a subject or animal. Therapeutic treatment thus includes inhibiting the disease or condition and/or the adverse events associated with the disease or condition, e.g. arresting its/their development; and relieving the disease or condition and/or adverse events associated with the disease or condition, causing regression of the disease or condition and/or of the adverse events associated with the disease or condition. The present disclosure considers such prophylactic and/or therapeutic treatment for *Varroa destructor* mite infestation(s) of bees and/or bee hives.

For the purposes of the present disclosure it should be understood that phrases like "Compound X for use in prophylactic and/or therapeutic treatment of . . . ", "Use of compound X in the manufacture of a composition for prophylactic and/or therapeutic treatment of . . . ", or "Method of prophylactic and/or therapeutic treatment of . .

. . By applying compound X to . . . " all circumscribe that a compound X (such as in the present case lithium chloride) is used for a specific prophylactic and/or therapeutic purpose (such as in the present case the prophylactic and/or therapeutic treatment of *Varroa destructor* infestation of honey bees.

As is described in the experiments further below, the present disclosure originally set out to develop siRNA molecules which could be used to treat *Varroa destructor* infestation of bee hives. To this end, double stranded (ds) RNA molecules of approx. 500 bp in length against *Varroa destructor*-specific genes were designed and fed to honeybees in 50% sucrose solution. As a negative control non-specific dsRNA was used. In contradiction to the results reported by Garbian et al. (Garbian Y, Maori E, Kalev H, Shafir S, Sela I. Bidirectional Transfer of RNAi between Honey Bee and *Varroa destructor*: *Varroa* Gene Silencing Reduces *Varroa* Population. Schneider D S, ed. PLoS Pathogens. 2012; 8(12):e1003035. doi:10.1371/journal.ppat.1003035.) no differences in efficacy were seen between the negative control dsRNA and the *Varroa destructor*-specific dsRNAs when the negative control siRNA and pools of specific dsRNAs were fed to the bees at equal amounts. Subsequently, it was found out that a component which had been used during purification of dsRNAs, namely lithium chloride has the capacity to act as a miticide against *Varroa destructor* infestation of bee hives. The present disclosure thus identifies and establishes lithium chloride as a miticide, preferably against *Varroa destructor* infestation of bees. Against this background it seems reasonable to assume that other salts of lithium and other alkali metal salts can act as miticides, preferably against *Varroa destructor* infestation of bees.

In a first aspect, the present disclosure thus relates to the use of alkali metal salts as a miticide. Lithium salts are the preferred alkali metal salts and the most preferred miticidal use for alkali metal salts, preferably lithium salts, is against *Varroa destructor*. Lithium chloride is the most preferred alkali metal salt and the most preferred miticidal use for alkali metal salts, most preferably lithium chloride, is against *Varroa destructor* infestation of honey bees.

A second aspect relates to an alkali metal salt for use as a miticide. Lithium salts are the preferred alkali metal salts and the most preferred miticidal use for alkali metal salts, preferably lithium salts, is against *Varroa destructor* infestation of honey bees. Lithium chloride is the most preferred alkali metal salt and the most preferred miticidal use for alkali metal salts, most preferably lithium chloride, is against *Varroa destructor* infestation of honey bees.

A third aspect relates to the use of an alkali metal salt in the manufacture of a miticidal composition (which can also be designated as a medicinal composition) for prophylactic and/or therapeutic treatment of a mite infestation. Lithium salts are the preferred alkali metal salts and the most preferred prophylactic and/or therapeutic treatment of mite infestation relates to the prophylactic and/or therapeutic treatment of *Varroa destructor* infestation of honey bees. Lithium chloride is the most preferred alkali metal salt and the most preferred prophylactic and/or therapeutic preferred treatment of mite infestation relates to the prophylactic and/or therapeutic treatment of *Varroa destructor* infestation of honey bees.

A fourth aspect relates to a method of prophylactic and/or therapeutic treatment of a mite infestation by applying an alkali metal salt to a bee suffering from a mite infestation or being suspected of a mite infestation. Lithium salts are the preferred alkali metal salts and the most preferred prophylactic and/or therapeutic treatment of mite infestation relates to the prophylactic and/or therapeutic treatment of *Varroa destructor* infestation of honey bees. Lithium chloride is the most preferred alkali metal salt and the most preferred prophylactic and/or therapeutic preferred treatment of mite infestation relates to the prophylactic and/or therapeutic treatment of *Varroa destructor* infestation of honey bees.

A fifth aspect relates to a method of manufacturing a miticidal composition comprising at least the steps of
a) providing an alkali metal salt in a concentration which is effective as a miticide,
b) optionally combining said alkali metal salt with further excipients, and
c) optionally adding the alkali metal salt of step a) and the further excipients of step b) to a bee-ingestible composition.

Lithium salts are the preferred alkali metal salts. Lithium chloride is the most preferred alkali metal salt and the bee-ingestible composition may be a bee-ingestible nutritional solution. Such miticial composition can be used for prophylactic and/or therapeutic treatment of *Varroa destructor* infestation of honey bees.

In the following specific embodiments are discussed for the first, second, third, fourth and fifth aspect of the present disclosure. It should be understood that the following considerations equally apply to all of the aforementioned aspects. It should be further understood that for any of the aspects discussed hereinafter the preferred alkali metal salts are lithium salts, the most preferred alkali metal salt is lithium chloride, and the most preferred miticidal use is against *Varroa destructor* infestations of honey bees.

It should be understood that whenever a reference is made to alkali metal salts or lithium salts, such alkali metal salts or lithium salts comprise any organic as well as inorganic salts of alkali metals or lithium which are suitable for and capable of exerting a miticidal effect, preferably on *Varroa destructor* infestation of honey bees.

Organic salts of alkali metals such as lithium include salts such as the citrate salt, carbonate salt, lactate salt, formate salt, acetate salt, trifluoroacetate salt, maleate salt, tartrate salt, orotate salt and the like. Inorganic acid salts of alkali metals include salts such as the fluoride salt, chloride salt, bromide salt, sulfate salt, phosphate salts and the like. For the purposes of the present description, inorganic salts can be preferred over organic salts. Within the group of inorganic salts, the halides can be preferred over other inorganic salts. Within the halides, the chloride salt can be particularly preferred. Irrespective of which salts are used (organic salts versus inorganic salts, etc.), water-soluble salts are preferred as they can be provided in the form of a bee-indigestible composition such as sucrose solutions which can be fed to the bees and thus taken up indirectly by the *Varroa* mites through this route. Whenever reference is made to a specific salt, it always includes the hydrated or anhydrous versions thereof unless indicated otherwise.

The group of alkali metals comprises lithium, sodium, potassium, rubidium and caesium. Within the group of alkali metals, lithium is particularly preferred.

As a consequence, of the alkali metal salts considered by the present disclosure organic or inorganic salts of lithium which may be hydrated or anhydrous are preferred over the corresponding salts of e.g. potassium. Inorganic lithium salts such as LiCl are advantageous because they cost less as compared to organic lithium salts. Within the group of lithium salts, inorganic lithium salts can thus be preferred over organic lithium salts. Preferred inorganic lithium salts include but are not limited to lithium chloride, lithium bromide, lithium nitrate, lithium sulfate, lithium phosphate and the like. However, organic lithium salts can be advantageous because they may complex more than one lithium ion and because they may be taken up by the bees better as compared to inorganic lithium salts. Preferred organic lithium salts include but are not limited to lithium citrate, lithium carbonate, lithium lactate, lithium formate, lithium acetate, lithium trifluoroacetate, lithium maleate, lithium tartrate, lithium orotate and the like. Within the group of inorganic lithium salts, the halides can be preferred over other inorganic salts. Within the group of organic lithium salts, the lactates, citrates, acetates and carbonates can be preferred over other organic salts.

One alkali metal salt which is preferred throughout all aspects and embodiments described hereinafter is lithium chloride in hydrated or anhydrous form.

As will transpire from the experiments described hereinafter lithium chloride is effective in killing *Varroa destructor* mites on honey bees. It further transpires from the experiments described hereinafter that a "miticidal window" exists for lithium chloride in which *Varroa destructor* infestation is reduced without significantly affecting the health of the honey bees.

This "miticidal window" ranges from about 0.5 mM to about 150 mM lithium chloride when lithium chloride is provided in the form of the bee-ingestible or liquid composition ad libidum. This concentration range of lithium chloride is calculated on the basis of anhydrous lithium chloride. Further experiments have shown that the miticidal effect of lithium chloride, preferably when used for prophylactic and/or therapeutic treatment of *Varroa destructor* infestation improves when being raised from the lower end of the aforementioned concentration range, i.e. from about 1 mM towards higher numbers within the concentration range of about 1 mM to about 150 mM lithium chloride. However, when being used at higher concentrations preliminary data indicate that the health of the bees might at least transiently be affected. Currently, concentration ranges from about 2 mM to about 125 mM, from about 2 mM to about 100 mM, from about 2 mM to about 90 mM, from about 2 mM to about 80 mM, from about 2 mM to about 75 mM lithium chloride seem to represent a good compromise between miticidal activity without negatively impairing the health of the bees. From the observations in the experiments and the aforementioned considerations it transpires that the range of about 2 mM to about 75 mM lithium chloride can be preferred over the range of about 1 mM to about 150 mM lithium chloride. The miticidal window may even more preferably consider concentrations such as about 2 mM, about 10 mM, about 15 mM, about 20 mM, about 25 mM, about 30 mM, about 35 mM, about 40 mM, about 45 mM, about 50 mM, about 55 mM or about 60 mM lithium chloride or any concentration ranges arising from the aforementioned specific concentrations of about 2 mM to about 60 mM lithium chloride. It needs to be understood that all of the aforementioned concentrations refer to concentration values calculated for anhydrous lithium chloride dissolved in a bee-ingestible composition such as a 70% sucrose solution. If specific hydrated salts of lithium chloride are to be used, concentrations being equimolar equivalents of the aforementioned concentrations for anhydrous lithium chloride should be used. Equimolar equivalents should be calculated based on lithium since lithium is considered the miticidal agent. If specific organic or inorganic lithium salts are to be used, concentrations being equimolar equivalents of the aforementioned concentrations for anhydrous lithium chloride should be used with respect to the lithium ion. For example, one citrate molecule is capable of complexing three lithium ions which needs to be considered when calculating equimolar amounts.

In general, the period of treatment of the bees with lithium chloride will depend on the concentration of lithium chloride used. Lower concentrations such as 1 mM LiCl may afford a longer treatment period than 25 mM but are also effective in killing *Varroa* mites. Based on the cage experiments, it seems reasonable to treat bee hives with 2 to 70 mM, preferably 20 to 60 mM and more preferably with 25 to 50 mM. A reasonable treatment period derived from the cage experiments is 2 to 21 days, preferably 4 to 14 days, more preferably 5 to 9 days and most preferably 7 days.

It should be further understood that the aforementioned concentration range was determined in bee cages with 100 bees and 30 mites. The concentration range for the miticidal window may shift to lower, higher or broader concentration ranges once one is treating a complex population of different honey bees and larval stages in a natural hive. However, the aforementioned concentration ranges establish that miticidal windows exist and provide guidance for identifying miticidal windows for specific applications.

If lithium chloride is not provided as a liquid bee-ingestible composition, but for example as a solid composition or a nebulized composition which is sprayed into the bee hive the concentration can be straightforwardly determined using experiments as described below. Nevertheless, the aforementioned concentration ranges may be a good starting point for calculating starting test concentrations of lithium chloride if other routes of administration are considered than liquid bee-indigestible compositions. The same applies if other salts of lithium than lithium chloride are considered.

The present disclosure contemplates for all aspects and embodiments thereof to use alkali metal salts, preferably lithium salts and most preferably lithium chloride at concentrations within this miticidal window.

The alkali metal salts, preferably lithium salts, most preferably lithium chloride can be used for prophylactic and/or therapeutic treatment of mite infestations, most preferably *Varroa destructor* infestations of honey bees in the form of bee-ingestible compositions such as liquid compositions. They may also be provided as solid compositions, semi-solid compositions such as feedpaste, or compositions which can be sprayed in bee hives.

Compositions comprising alkali metal salts, preferably lithium salts, most preferably lithium chloride and more preferably liquid nutritional compositions which can be fed to the bees may comprise further components such as sucrose, corn syrup, pollen, starch syrup, and/or other nutritional factors so that administration of the alkali metal salts, preferably lithium salts, most preferably lithium chloride and feeding the bees takes place simultaneously.

Liquid nutritional compositions such as sucrose solutions which can be fed to the bees are particularly preferred. Sucrose solutions can comprise e.g. about 40% to about 80% sucrose such as about 50%, about 60% or about 70% sucrose.

Compositions which are used to administer the alkali metal salts, preferably the lithium salts, most preferably lithium chloride, to the mites such as liquid compositions which are bee-ingestible can comprise the alkali metal salts, preferably lithium salts, most preferably lithium chloride as the sole miticidal agent. In other embodiments, the compositions may further comprise additional miticides as they are already used for treatment of e.g. *Varroa destructor* infestations of honey bees such as fluvalinate or chemicals such formic acid, oxalic acids, etc.

However, alkali metal salts, preferably lithium salts, most preferably lithium chloride may also be added to pesticidal, herbicidal or fungicidal compositions that are used in agricultural production and are for example applied to crops, fruits, nuts, etc. By adding alkali metal salts, preferably lithium salts, most preferably lithium chloride, to these types of compositions, bees may take up the alkali metal salts upon pollination and may thus be either therapeutically treated for already existing *Varroa destructor* infestations or be prophylactically protected against such infestations.

The bees to be treated can be of the genus *Apis mellifera* or *Apis cerana*. Bees to be treated include all bees of a honey bee population, i. e. foragers and hive bees, and honey bee larvae of yet unsealed brood cells.

The alkali metal salts, preferably lithium salts, most preferably lithium chloride may ideally be administered to said bees during phases of decreased egg-laying by the queen bee. Such a phase of decreased egg-laying starts in the northern hemisphere after the calendar start of summer in June and becomes more pronounced in late autumn, preferably in September, October and November till December of each year.

In other regions of the world this effect may be less pronounced but application of alkali metal salts, preferably lithium salts, most preferably lithium chloride should in general commence if there is at least comparatively decreased egg-laying activity.

Further preferred embodiments of the present invention relate to:

1. An alkali metal salt for use in prophylactic and/or therapeutic treatment of *Varroa destructor* mite infestation of honey bees.
2. An alkali metal salt for use according to 1, wherein said alkali metal salt is provided as a bee-ingestible composition or a sprayable composition.
3. An alkali metal salt for use according to 2, wherein said bee-ingestible composition is in liquid form or is a feedpaste.
4. An alkali metal salt for use according to 3, wherein said liquid bee-ingestible composition is a nutritional solution which optionally comprises sucrose, corn syrup, and/or starch syrup.
5. An alkali metal salt for use according to 2, 3, or 4, wherein said bee-ingestible composition comprises said alkali metal salt in a concentration range which is equimolar to the concentration range of about 1 to about 150 mM LiCl anhydrous.
6. An alkali metal salt for use according to 2, 3, 4, or 5, wherein said bee-ingestible composition comprises said alkali metal salt in a concentration range which is equimolar to the concentration range of about 5 to about 100 mM LiCl anhydrous.
7. An alkali metal salt for use according to 2, 3, 4, 5, or 6, wherein said bee-ingestible composition comprises said alkali metal salt in a concentration range which is equimolar to the concentration range of about 10 to about 75 mM LiCl anhydrous.
8. An alkali metal salt for use according to 1, 2, 3, 4, 5, 6, or 7, wherein said alkali metal salt or said bee-ingestible composition comprising said alkali metal salt or said sprayable composition comprising said alkali metal salt is administered to said bees.
9. An alkali metal salt for use according to 1, 2, 3, 4, 5, 6, 7, or 8, wherein said alkali metal salt is a water-soluble salt.
10. An alkali metal salt for use according to 1, 2, 3, 4, 5, 6, 7, 8, or 9, wherein said alkali metal salt is LiCl anhydrous or hydrated forms thereof.
11. An alkali metal salt for use according to 1, 2, 3, 4, 5, 6, 7, 8, 9, or 10, wherein said bees are of the genus *Apis*, species *Apis mellifera* or *Apis cerana*.
12. An alkali metal salt for use according to 1, 2, 3, 4, 5, 6, 7, 8, 9, 10, or 11, wherein said bees are honeybees, i. e. foragers and/or hive bees and unsealed honey bee larvae.
13. Use of an alkali metal salt for prophylactic and/or therapeutic treatment of *Varroa destructor* mite infestation of honey bees.
14. Use of an alkali metal salt in the manufacture of a composition for prophylactic and/or therapeutic treatment of *Varroa destructor* mite infestation of honey bees.
15. Method of prophylactic and/or therapeutic treatment of *Varroa destructor* mite infestation of honey bees, the method comprising administering an alkali metal salt to said bees.
16. Use according to 13 or 14 or method of claim 15, wherein said alkali metal salt is provided as a bee-ingestible composition or sprayable composition.
17. Use or method according to 16, wherein said bee-ingestible composition is in liquid form.
18. Use or method according to 17, wherein said liquid bee-ingestible composition is a nutritional solution which optionally comprises sucrose, corn syrup, and/or sucrose syrup.
19. Use or method according to 16, 17, or 18, wherein said bee-ingestible composition comprises said alkali metal salt in a concentration range which is equimolar to the concentration range of about 1 to about 150 mM LiCl anhydrous.
20. Use or method according to 16, 17, 18, or 19, wherein said bee-ingestible composition comprises said alkali metal salt in a concentration range which is equimolar to the concentration range of about 5 to about 100 mM LiCl anhydrous.
21. Use or method according to 16, 17, 18, 19, or 20, wherein said bee-ingestible composition comprises said alkali metal salt in a concentration range which is equimolar to the concentration range of about 10 to about 75 mM LiCl anhydrous.
22. Use or method according to 16, 17, 18, 19, 20, or 21, wherein said alkali metal salt or said bee-ingestible composition comprising said alkali metal salt is administered to said bees.
23. Use or method according to 16, 17, 18, 19, 20, 21, or 22, wherein said alkali metal salt is a water-soluble salt.
24. Use or method according to 16, 17, 18, 19, 20, 21, 22, or 23, wherein said alkali metal salt is LiCl anhydrous or hydrated forms thereof.
25. Use or method according to 16, 17, 18, 19, 20, 21, 22, 23, or 24, wherein said bees are of the genus *Apis* with species *Apis mellifera* or *Apis cerana*.
26. Use or method according to 16, 17, 18, 19, 20, 21, 22, 23, 24, or 25, wherein said bees are honeybees, foragers, and/or hive bees.
27. Use of lithium chloride as a miticide against *Varroa destructor* infestation of bees.

FIGURE LEGENDS

Figure 2:
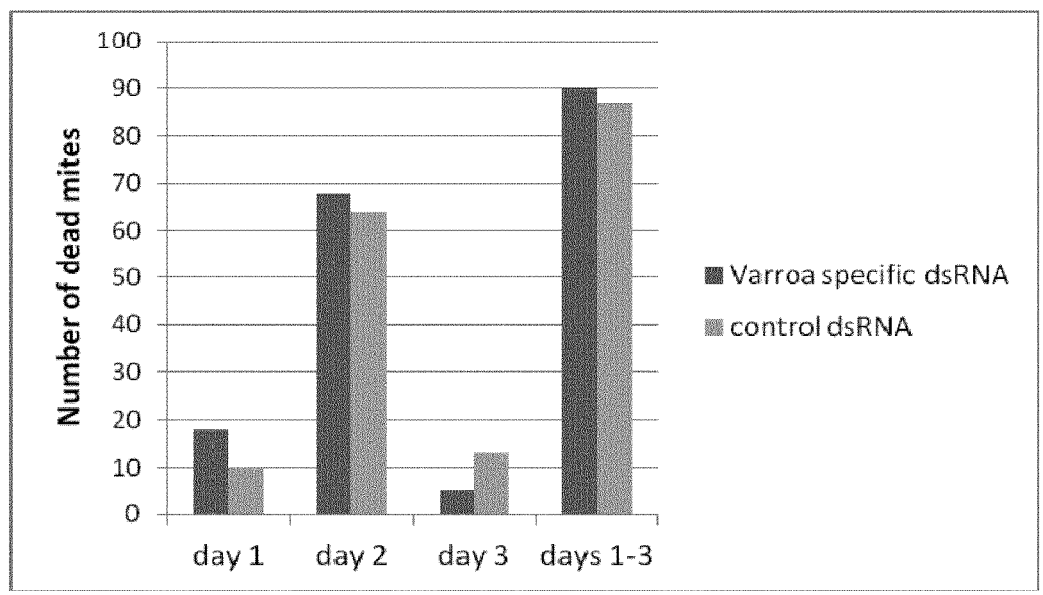

FIG. 1: depicts cage in which 100 bees were kept with 30 *Varroa destructor* mites and feed with sucrose solution comprising either dsRNA or lithium chloride FIG. 2: depicts number of dead mites after treatment with *Varroa destructor* specific dsRNAs or non-specific control RNAs. 100 bees were placed with 30 *Varroa* mites in 1 cage and treated as indicated in Experiment 1. FIG. 2 depicts the combined results from 3 cages for either *Varroa destructor* specific dsRNAs or non-specific control RNAs.

Figure 3:
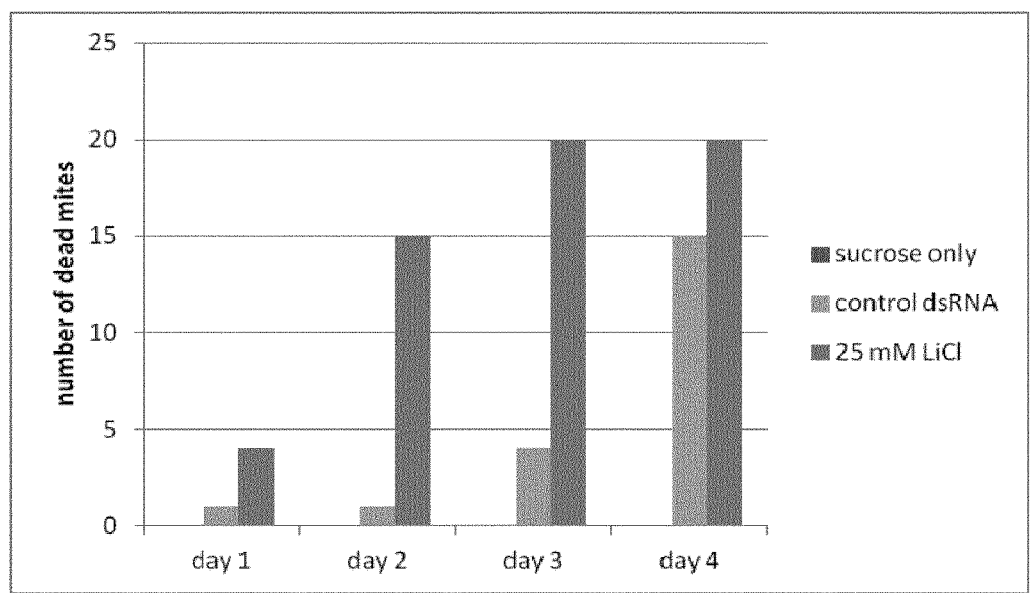

FIG. 3 depicts number of dead mites after treatment with 70% sucrose solution only, non-specific control dsRNAs or 25 mM LiCl in 70% sucrose solution. 100 bees were placed with 30 *Varroa* mites in 1 cage and treated as indicated in Experiment 2. FIG. 3 depicts the results for either sucrose only treatment, non-specific control dsRNAs or 25 mM LiCl.

Figure 4:
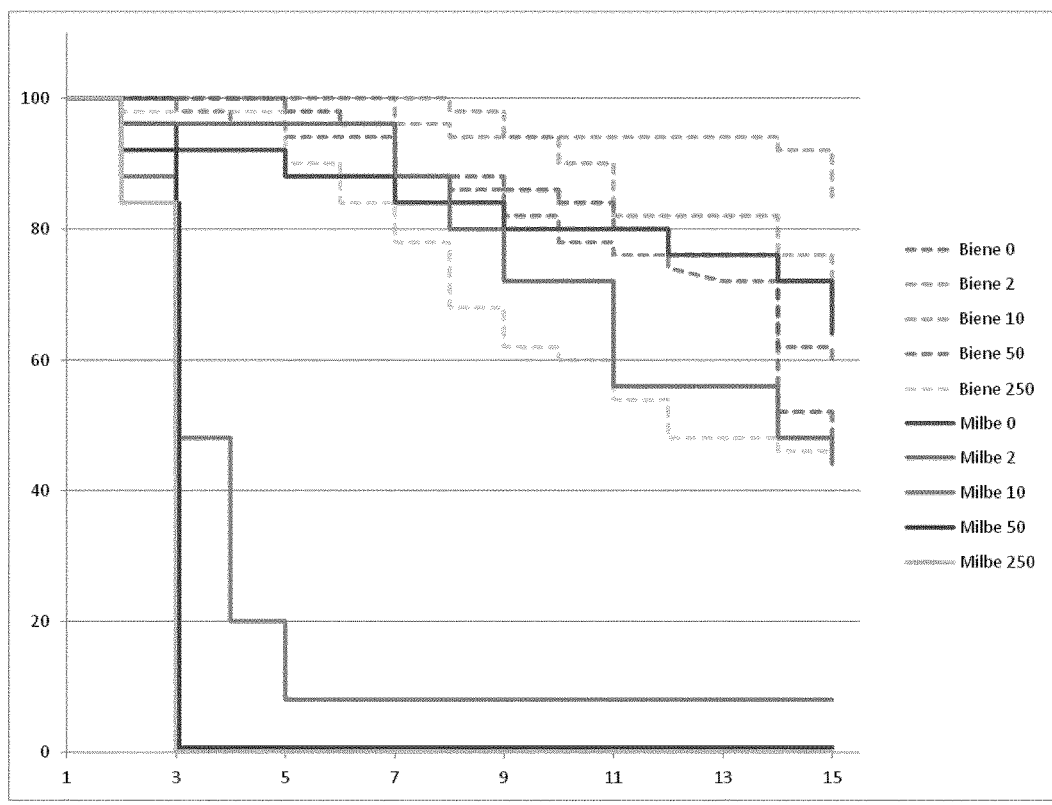

FIG. 4: Kaplan-Meyer Plot of bees and *Varroa* mites in percentages. Dashed lines indicate bees, straight line indicate mites. Numbers 0, 2, 10, 50, and 250 indicate concentrations of 0 mM, 2 mM, 10 mM, 50 mM and 250 mM LiCl in the sucrose solution. The Y-axis indicates percent of surviving bees and mites. The X-axis indicates days after starting feeding LiCl. "Biene" stands for bee and "Milbe" stands for mite.

Figure 5:
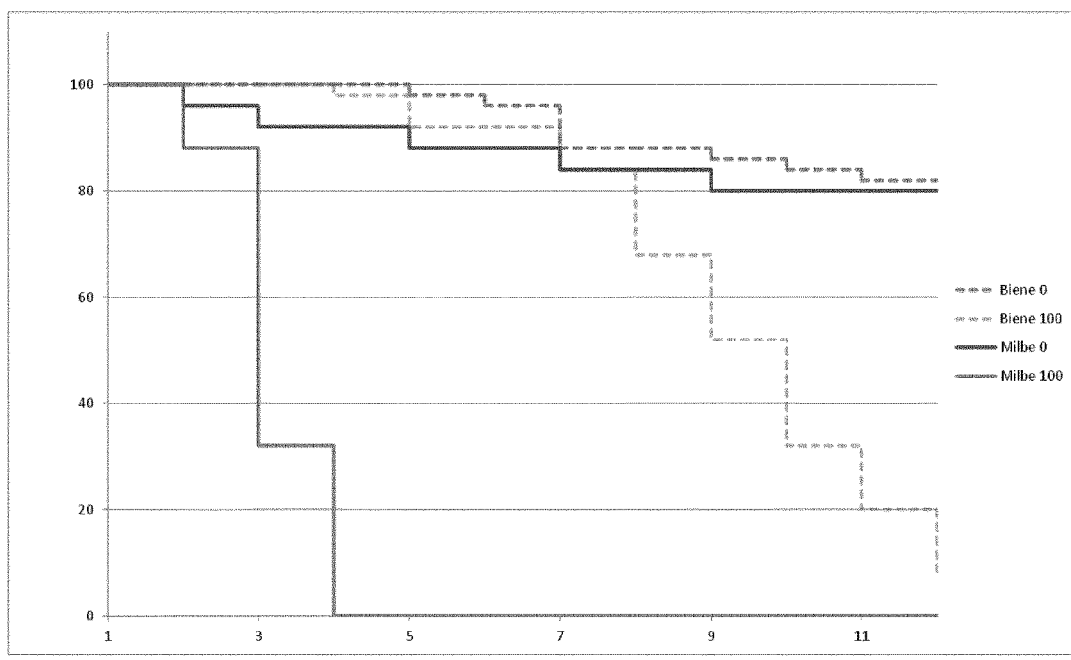

FIG. 5: Kaplan-Meyer Plot of bees and *Varroa* mites in percentages. Dashed lines indicate bees, straight line indicate mites. Numbers 0 and 100 indicate concentrations of 0 mM and 100 mM LiCl in the sucrose solution. The Y-axis indicates percent of surviving bees and mites. The X-axis indicates days after starting feeding LiCl. "Biene" stands for bee and "Milbe" stands for mite.

Figure 6:
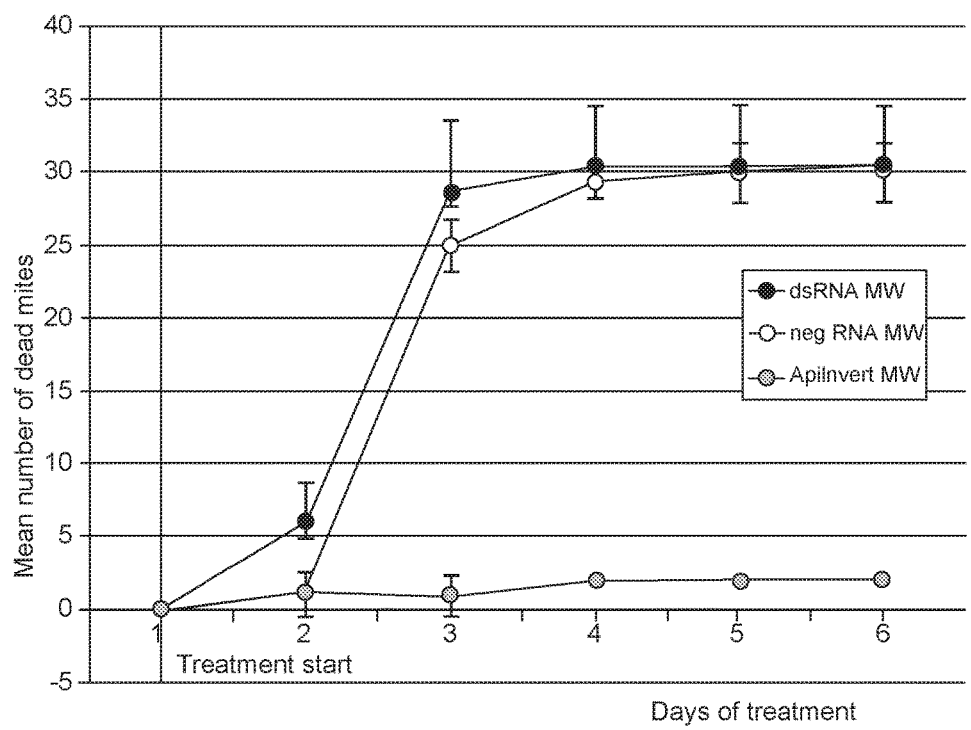

FIG. 6: depicts mean number of dead mites with standard deviation after treatment with *Varroa destructor* specific dsRNAs ("ds RNA MW") or non-specific control RNAs ("neg RNA MW"). A control with 70% sucrose solution only is also included ("ApiInvert MW"). Results represent mean values derived from three cages whereby 100 bees were placed with 30 *Varroa* mites in 1 cage and treated as indicated in Experiment 1.

Figure 7:
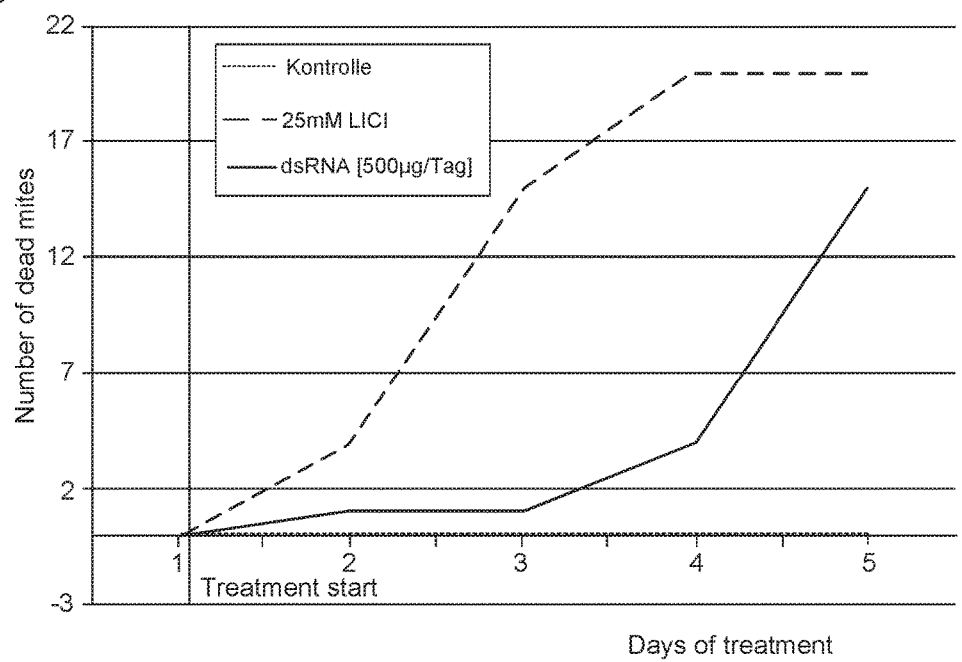

FIG. 7: depicts number of dead mites after treatment with 70% sucrose solution only ("Kontrolle"), non-specific control dsRNAs ("dsRNA [500 µg/Tag]") or 25 mM LiCl in 70% sucrose solution ("25 mM LiCl"). 100 bees were placed with 30 *Varroa* mites in 1 cage and treated as indicated in Experiment 2.

Figure 8:
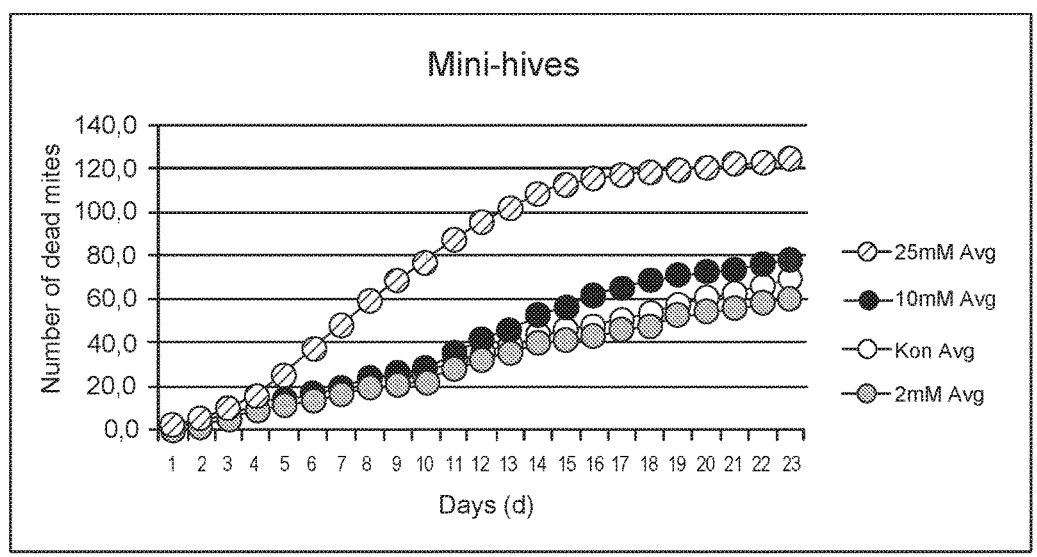

FIG. 8: depicts the mean number of dead mites upon treatment with 70% sucrose solution only ("Kon Avg"), 2 mM LiCl in 70% sucrose solution ("2 mM Avg"), 10 mM LiCl in 70% sucrose solution ("10 mM Avg") or 25 mM LiCl in 70% sucrose solution ("25 mM Avg") over a treatment period of 23 days.

DETAILED DESCRIPTION OF THE INVENTION

The following examples illustrate specific embodiments of the aspects described above. They are not to be construed as limiting.

Experiment 1—siRNA Approach to Fight *Varroa destructor* Infestation

The publication of Garbian et al. (Garbian Y, Maori E, Kalev H, Shafir S, Sela I. Bidirectional Transfer of RNAi between Honey Bee and *Varroa destructor: Varroa* Gene Silencing Reduces *Varroa* Population. Schneider D S, ed. PLoS Pathogens. 2012; 8(12):e1003035. doi:10.1371/journal.ppat.1003035) showed that dsRNA complementary to essential genes in *Varroa destructor* could be used to combat varroosis. DsRNA was dissolved in glucose syrup and fed to bees and subsequently taken up by parasitizing mites via the bees' hemolymph. The publication suggested that ingested dsRNA could knock down the respective *Varroa* genes by a systemic RNAi based mechanism.

In a first experiment a refined list of potentially essential *Varroa* genes was assembled and dsRNA molecules were synthesized. In a first experiment, a refined list of potentially essential *Varroa* genes was assembled and dsRNA molecules were synthesized. The refined list was generated by retrieving essential genes from various eukaryote species (fly, worm, human, zebrafish) (http://ogeedb.embl.de). Where possible, homologous genes were determined using NCBI HomoloGene DB. Then genes from *Drosophila* with homology to the Contig sequences published by Comman et al were identified. (Comman et al.: http://www.ncbi.nlm.nih.gov/pubmed/20973996). The identified genes were ranked according to the number of species where they were essential.

To generate the respective dsRNA, *Varroa* RNA was extracted and used to generate cDNA. Specific primers were designed to synthesize dsRNA by in vitro transcription and subsequent hybridization. Primer sequences for the respective genes were based on the sequence of the fly database which can be found at http://flybase.org. The list comprised the following genes:

TABLE 1

| Fly_symbol | Flybase accession no. | human_description | Human symbol |
|---|---|---|---|
| RPN1* | FBgn0028695 | proteasome (prosome, macropain) 26S subunit | PSMD2 |
| RPN3* | FBgn0261396 | proteasome (prosome, macropain) 26S subunit | PSMD3 |
| NOI* | FBgn0014366 | splicing factor 3a, subunit 3, 60 kDa | SF3A3 |
| CG2807* | FBgn0031266 | splicing factor 3b, subunit 1, 155 kDa | SF3B1 |
| RPL7* | FBgn0005593 | ribosomal protein L7 | RPL7 |
| ATPsyn* | FBgn0010217 | ATP synthase, H+ transporting, mitochondrial F1 complex, beta polypeptide | ATP5B |
| Tbp1 | FBgn0028684 | proteasome (prosome, macropain) 26S subunit, ATPase, 3 | PSMC3 |
| AlphaTub* | FBgn0003884 | tubulin, alpha 1c | TUBA1C |
| His2B* | FBgn0061209 | histone cluster 1, H2bj | HIST1H2BJ |
| RPT4 | FBgn0028685 | proteasome (prosome, macropain) 26S subunit, ATPase, 6 | PSMC6 |
| Pros26.4 | FBgn0015282 | proteasome (prosome, macropain) 26S subunit, ATPase, 1 | PSMC1 |
| PP2A-B | FBgn0042693 | protein phosphatase 2, regulatory subunit B', delta | PPP2R5D |
| RPL15* | FBgn0028697 | ribosomal protein L15 | RPL15 |
| RPN2 | FBgn0028692 | proteasome (prosome, macropain) 26S subunit, non-ATPase, 1 | PSMD1 |
| Blw* | FBgn0011211 | ATP synthase, H+ transporting, mitochondrial F1 complex | ATP5A1 |
| So* | FBgn0003460 | SIX homeobox 1 | SIX1 |
| Med* | FBgn0011655 | SMAD family member 4 | SMAD4 |

DsRNA was precipitated using standard procedures and lyophilized. RNA was provided at 1 µg/µl. As control dsRNA corresponding to human GAPDH was synthesized, hybridized and purified. Alternatively, a mix of uncleaved siPOOL dsRNA (as described in WO 2013/160393 A1) not targeting any gene in the human genome was used as negative control.

12 genes were selected for a first experiment (marked with an asterisk in Table 1).

In accordance to Garbian et al. (vide supra), 100 bees were kept in a container and 30 mites were added to each container (see FIG. 1). Bees were fed 80 µg per gene and day. In view of 12 genes this adds up to 960 µg of dsRNA per container and day dissolved in 2 ml of 70% sucrose solution. In the publication of Garbian et al. (vide supra), the experiments were carried out with 2 different dsRNA mixes, with each mix comprising 200 µg of either 5 or 14 different dsRNA species targeting different Varroa genes in 5 ml sucrose solution. As such, different total amounts of dsRNA were fed to each test hive. Moreover, control experiments were carried out with either sucrose solution only or unrelated dsRNA encoding GFP. The GFP control however was carried out with only 200 µg total dsRNA in 5 ml sucrose solution exposing the bees to less dsRNA irrespective of its nucleotide sequence.

Other than Garbian et al. (vide supra) we choose to control our experiments with similar total amounts of control RNA to exclude a sequence unspecific effect of dsRNA on the mites.

3 cages with each cage having 100 bees/30 mites were treated with 12 dsRNA species, 80 µg per gene and day over a period of 6 days. Dead mites and bees were collected and counted. In parallel 3 cages were treated with unrelated control dsRNA at corresponding total amount of dsRNA. Additionally, 2 cages were treated with sucrose solution only.

In cages treated with dsRNA targeting mite-specific genes, mites were killed effectively within the first 2 days. Complete loss of mites was observed after 3 days (day 1: 18 mites, day 2: 68 mites, day 3: 5 mites, see FIG. 2 for combined results or see FIG. 6 for mean numbers of dead mites per treatment day). Interestingly a similar response was found in mites fed with sucrose containing dsRNA not targeting any gene in Varroa (day 1: 10 mites, day 2: 64 mites, day 3: 13 mites, day 4: 2 mites, see FIG. 2 for combined results or see FIG. 6 for mean numbers of dead mites per treatment day).

In summary, all mites in either treatment regimen were killed within the first 3 days of treatment and a difference in response to either treatment could not be observed. Cages treated with sucrose alone did not show any response. Of note, bees showed toxicity effects starting from day 3 and around 30% of the bees were lost within the first 6 days of treatment (data not shown). Bees and mites in cages that were fed sucrose without RNA did not exhibit any toxicity responses.

Experiment 2—Identification of Lithium Chloride as Miticide Against Varroa destructor Based on the observations in Experiment 1 we reasoned that effects of dsRNA did not relate to the sequence and maybe a non-specific response to dsRNA or agents copurifiying with dsRNA in the production process.

To reproduce the observation, the experiment was repeated with the negative control dsRNAs and the results confirmed the findings of Experiment 1 lending support to an unspecific RNA effect.

Additionally, we set out to pursue the question of potentially copurifying toxic agents. In the dsRNA production process dsRNA is precipitated with LiCl at 7.5M. We reasoned that even after extensive washing substantial amounts of lithium may be present in the RNA samples. In view of 2 washes with 70% EtOH after precipitation we considered 25 mM LiCl a reasonable concentration to integrate into the experiment.

The next set of experiments was carried out in plastic container with 50 bees and 20 mites each. Bees were fed the same amount of unspecific dsRNA that has been used in previous assays in 70% sucrose solution, LiCl at a concentration of 25 mM in 70%, sucrose solution, and 70% sucrose solution only.

Bees and mites in cages supplied with sucrose syrup only did not show an impact on viability of either mite or bee.

Cages that were fed sucrose containing dsRNA that has been subjected to extensive washing displayed activity against Varroa destructor but was tolerated well by the bees. After 24 h only one mite was killed and a total of 4 mites were dead after 72 hours. After 4 days 75% of the mites were killed, indicating a decreased activity compared to the results from the previous experiments where identical concentrations of ds RNA was fed to the bees. No bees were affected.

LiCl at a concentration of 25 mM however displayed high activity against Varroa destructor, with 4 mites dead after 24 h, 15 and 20 after 48 and 72 h of treatment, respectively. Bees however were not affected within the first 4 days of treatment with 25 mM LiCl.

The results are summarized in FIG. 3 as a bar graph and in FIG. 7 as a line graph.

Experiment 3—Dose Response Relation of Lithium Chloride as Miticide Against Varroa destructor To analyze the therapeutically active concentrations of LiCl in more detail we devised a series of experiments in cages of 50 bees to each of which 25 mites were added. LiCl was added to 70% sucrose solution to final concentrations of 16 µM, 80 µM, 400 µM, 2 mM, 10 mM, 50 Mm, and 250 mM, respectively. 2 ml of the respective solution was fed to the bees, if the sucrose/LiCl solution was entirely ingested additional sucrose syrup was offered ad libidum. Uptake of LiCl solution as well as survival rate of bees and mites was monitored 3 times daily (morning, noon, evening). Additionally, the healthiness of bees was scored based on characteristic behavioral features. LiCl was administered until all mites were dead, and the experiment continued with plain sucrose syrup to record the response of bees over the entire 2 weeks of the experiment. For control bees treated with sucrose syrup only, 9 mites died within the course of the experiment with even timely distribution of the events, indicating natural death of mites. 26 bees died in the same period of time. In view of the life span of a worker bee (4 weeks) this relates to the natural death rate that can be expected in a time span of 14 days. However, 12 bees were lost in a single day equaling almost 50% of the total bee loss in this control experiment. Moreover, bees treated with LiCl up to 50 mM did not exhibit comparable responses. For that reasons the sudden loss of bees on day 14 is considered to result from a mistake in bee treatment as feeding inappropriate amounts of sucrose syrup. (See FIG. 4, dotted red line)

Cages that were fed sucrose with 250 mM LiCl lost all mites within the first 48 hours of the experiment, the majority of which (21/25) within the timespan between 30 h and 48 h. Bees were fed sucrose syrup only after all mites were dead and the viability of bees was monitored for the remaining experiment. 27 bees were lost in total with an average rate of 3 bees per day, indicating a toxic effect on bees even after treatment was terminated and bees were fed sucrose only (FIG. 4, yellow lines)

A 5-fold decrease of LiCl to 50 mM LiCl in the sucrose syrup showed similar results with all mites dead after 48 h of treatment. Bee survival was similar with 20 bees lost in the timespan of the entire experiment. The average bee loss over time relates to the decay curve of controls until day 12 and thus indicates good tolerability by the bees (FIG. 4, purple lines).

Cages that were fed sucrose syrup with 10 mM LiCl showed delayed response compared to higher concentrated dosage. All mites were killed within the first 48 h of treatment (day 1: 3 mites, day 2: 10 mites, day 3: 7 mites, day 4: 3 mites, additionally 2 mites were found dead at the end of the experiment). The survival of bees improved over high concentrated LiCl to 34 bees alive at the end of the experiment (FIG. 4, green lines).

2 mM LiCl failed to kill all mites over the time span of the experiment but showed increased loss of mites compared to the control. 11 mites survived the treatment as well as 42 bees (FIG. 4, blue lines)

Lower concentrations only marginally impacted the viability of mites (data not shown). As such active concentrations of LiCl in cage experiments range between 2 mM and 250 mM. Bees tolerate a dosage of 2 mM LiCl over a period of 2 weeks without pronounced decrease in viability. Concentrations of 10 mM and higher exhibit a clear acaricidal effect and eliminate all mites within maximally 4 days.

These data are summarized for 0, 2, 10, 50 and 250 mM LiCl in FIG. 4.

Additionally, we set out to test activity of a single dose on mite viability. Sucrose with 25 mM LiCl was fed to a cage of 50 bees infested with 25 mites and monitored as described above. Mites were effectively killed within 72 h (3 mites were lost) and no negative impact on bee health could be observed over the course of the entire experiment. As such, a single dose of LiCl can be used to kill mites under the described conditions.

To explore the upper limit of dosage and limits of tolerability of bees we fed sucrose containing 100 mM of LiCl as only food source over 14 days. Again mites were effectively killed, however a time delayed continuous loss of bees showed toxicity of LiCl at high doses over a prolonged time of administration. In view of the latter results the effective window for concentration and administration and regimen of LiCl is sufficiently large to elevate low but effective concentrations (10 mM) more than 10 fold or prolong the time of administration substantially without negative impact on bee health. Taken together LiCl has been shown to exhibit strong acaricidal effects on *Varroa* mites without harming bees that can be administered systemically and such opens new opportunities to combat varroosis. The data is shown in FIG. 5.

Experiment 4—Test of Acaricidal Effect of MgCl2

To test the activity of bivalent ions we dissolved $MgCl_2$ in sucrose syrup at a final concentration of 100 mM. 2 cages of 50 bees to which 20 mites were added were fed with sucrose syrup only and syrup containing 100 mM $MgCl_2$. No impact on viability was seen for the control cage, however $MgCl_2$ appeared to impair bee health substantially. Moreover, only reduced amounts of sucrose syrup with $MgCl_2$ was taken up by the bees.

Experiment 5—Comparison of Acaricidal Effects of LiCl, NaCl and $MgCl_2$

In a further experiment LiCl, NaCl and $MgCl_2$ were selected and their acaricidal activity compared. The experiment was performed in cages of 50 bees, to each of which 25 mites were added. Bees in control cages received sucrose only. LiCl, NaCl or $MgCl_2$ were added to 70% sucrose solutions at a final concentration of 25 mM each and fed to the bees for seven days. Survival rate of bees and mites were monitored daily. Dead bees and mites were removed from the cages.

As can be seen from Table 2, column "Sum", only 3 of 50 bees died during treatment with LiCl while all mites were killed inferring a strong acaricidal effect. The numbers represent mean values derived from 6 cages. In contrast, during treatment with NaCl, 2 bees died while also only 2 mites died. The number of dead mites upon treatment with NaCl corresponds to the number of dead mites for the control which implies that NaCl fails to exhibit an acaricidal effect. As regards $MgCl_2$, all bees were dead after 5 days of treatment. Hence, $MgCl_2$ strongly impacts the viability of bees. Numbers for NaCl, $MgCl_2$ and control represent mean values derived from 3 separate cages.

Overall, the results of this experiment substantiate that lithium is the causative acaricidal agent.

TABLE 2

|  | Day | 1 | 2 | 3 | 4 | 5 | 6 | 7 | Sum |
|---|---|---|---|---|---|---|---|---|---|
| LiCl | Number of dead bees | 0.2 | 0.2 | 0.3 | 0.8 | 0.5 | 1.0 | 0.2 | 3.2 |
|  | Number of dead mites | 0.3 | 2.2 | 19.2 | 3.0 | 0.3 | 0.0 | 0.0 | 25.0 |
| NaCl | Number of dead bees | 0.0 | 0.0 | 0.0 | 0.3 | 0.0 | 0.0 | 1.3 | 1.7 |
|  | Number of dead mites | 0.0 | 0.3 | 0.0 | 0.0 | 0.3 | 0.7 | 1.0 | 2.3 |
| $MgCl_2$ | Number of dead bees | 0.0 | 18.0 | 18.3 | 9.3 | 4.3 | 0.0 | 0.0 | 50.0 |
|  | Number of dead mites | 0.3 | 1.0 | 1.0 | 3.7 | 0.7 | 0.0 | 0.0 | 6.7 |
| Control | Number of dead bees | 0.0 | 0.0 | 0.0 | 0.0 | 0.7 | 1.0 | 0.3 | 2.0 |
|  | Number of dead mites | 0.3 | 0.3 | 0.0 | 0.0 | 0.0 | 1.0 | 0.0 | 1.7 |

Experiment 6—Test of Acaricidal Effect of Various Lithium Salts

To test the acaricidal activity of further lithium salts, Li-citrate, Li-sulfate, Li-acetate, Li-lactate and Li-carbonate were dissolved in sucrose syrup at a final concentration of 25 mM. Each Li-salt was tested in cages of 50 bees to which 25 mites were added and replicated three times (results in Table 3 represent mean values). The bees were fed with Li-salt/sucrose solutions for 7 days. Survival rate of bees and mites were monitored daily and dead bees or mites were removed.

As can be seen from Table 3, bees treated with 25 mM Li-citrate, Li-sulfate, Li-acetate, Li-lactate or Li-carbonate lose all mites during the course of 7 days. The majority of mites is killed within the first 72 hours implying a high activity of said Li-salts against *Varroa destructor*.

TABLE 3

| Li-salt (25 mM) | Day | 1 | 2 | 3 | 4 | 5 | 6 | 7 | Sum |
|---|---|---|---|---|---|---|---|---|---|
| Li-sulfate | Number of dead bees | 0.0 | 0.0 | 0.0 | 1.0 | 3.7 | 1.7 | 0.0 | 6.3 |
|  | Number of dead mites | 0.7 | 18.0 | 5.7 | 0.7 | 0.0 | 0.0 | 0.0 | 25.0 |
| Li-citrate | Number of dead bees | 0.0 | 0.0 | 0.3 | 0.0 | 0.7 | 1.7 | 0.3 | 3.0 |
|  | Number of dead mites | 0.3 | 10.0 | 14.7 | 0.0 | 0.0 | 0.0 | 0.0 | 25.0 |
| Li-acetate | Number of dead bees | 0.0 | 0.0 | 0.3 | 0.3 | 0.3 | 0.7 | 1.0 | 2.7 |
|  | Number of dead mites | 0.7 | 14.0 | 10.3 | 0.0 | 0.0 | 0.0 | 0.0 | 25.0 |
| Li-lactate | Number of dead bees | 0.3 | 0.0 | 0.0 | 0.7 | 2.0 | 0.3 | 1.7 | 5.0 |
|  | Number of dead mites | 0.7 | 14.0 | 6.3 | 4.0 | 0.0 | 0.0 | 0.0 | 25.0 |
| Li-carbonate | Number of dead bees | 0.7 | 0.0 | 0.0 | 0.0 | 0.0 | 0.3 | 0.7 | 1.7 |
|  | Number of dead mites | 0.3 | 3.0 | 20.0 | 1.7 | 0.0 | 0.0 | 0.0 | 25.0 |

Interestingly, even lower concentrations of lithium salts (data not shown) effectively killed mites. 4 mM of Li-sulfate, Li-citrate, Li-acetate, Li-lactate and Li-carbonate killed all mites during the 7-day treatment period without a significant negative impact on bee viability.

Taken together, anorganic as well as organic lithium salts appear to exhibit a strong acaricidal effect on *Varroa* mites and might be valuable alternatives in the treatment of varroosis in bees.

Experiment 7—Acaricidal Effect of LiCl in Mini-Hives

In order to investigate if the miticidal effect of LiCl can also be detected under semi-field conditions, so-called "mini-hives" consisting of 2000 to 3000 bees each were treated with LiCl.

LiCl was dissolved in 70% sucrose to final concentrations of 2 mM, 10 mM and 25 mM. Each concentration was replicated 6 times and fed to the bees for 23 days. Dead mites were documented daily. After 23 days of LiCl treatment, remaining mites were killed with Perizin® (commercial product containing the active ingredient coumaphos) and counted (see Table 4 "Remaining mites").

As can be taken from FIG. 8 and Table 4, a majority of mites was killed for the 25 mM treatment group with only 24 mites left after LiCl treatment. Regarding a treatment with 10 mM LiCl, more mites are killed as compared to the control with only 54 mites remaining after LiCl treatment. A treatment with 2 mM LiCl appeared to have a similar mite fall as the control.

Overall, it can be inferred that a treatment with LiCl is effective against *Varroa destructor* infestation of bees under semi-field conditions and may be extended to natural hives.

TABLE 4

|  | Remaining mites |
|---|---|
| Control | 234 |
| 2 mM LiCl | 234 |
| 10 mM LiCl | 54 |
| 25 mM LiCl | 24 |

Experiment 8—The Effect of LiCl on Larval Development In Vitro

In order to assess the effect of LiCl on larval development in vitro, larvae were obtained by caging the queen for 24 h on broodless combs in the colony. After 5 to 6 days when the larvae reached the age of about 48 h they were transferred to petri dishes filled with larval food. The petri dishes were placed in plastic boxed filled with 8% sulfuric acid in order to prevent fungi infection and kept in a chamber at 34° C. and 95% relative humidity. The larvae were fed as needed with a mixture consisting of 53% royal jelly, 4% glucose, 8% fructose, 1% yeast extract and water (control). For samples treated with LiCl, 10 mM, 25 mM or 50 mM LiCl were added to the mixture. Prior to the pupa phase, the larvae were placed on a tissue for defecating which occurred approximately on day 9. Afterwards larvae were placed in well plates until hatching. Larvae mortality was monitored on a daily basis.

Table 5 summarizes the results expressed as survival rate of larvae or pupae. All larvae were lost within 72 hours implicating a strong lethal effect of LiCl on larvae. Since 25 mM LiCl is tolerated by bees very well but larvae viability is crucially impacted already at 10 mM LiCl, it follows that LiCl should ideally be applied when egg laying is decreased. Such a phase naturally occurs between the calender start of summer 6 and the overwintering period.

TABLE 5

|  | Survival rate (%) |
|---|---|
| Control | 51.2 |
| 10 mM LiCl | 0 |
| 25 mM LiCl | 0 |
| 50 mM LiCl | 0 |

Experiment 9—Artificial Swarms

Six artificial swarms were fed with sucrose/LiCl after a starving phase of several hours. LiCl was dissolved in sucrose at final concentrations of 25 mM and 50 mM. Each artificial swarm received 500 ml of the sucrose/LiCl mixture in a feeding balloon. The total volume of sucrose/LiCl solution was consumed by the bees. Mite fall was monitored for 7 days. Afterwards, bees were treated with Perizin® to assess the number of remaining mites.

As can be seen from Table 6, mites were effectively killed upon treatment of the bees with either 25 mM LiCl or 50 mM LiCl. A minority of mites was killed using Perizin® after the seventh day of LiCl treatment resulting in acaricidal efficacies of above 80% for all six swarms. Hence, it can be inferred that a treatment with LiCl will be effective against *Varroa destructor* infestation of natural bee hives under field conditions.

TABLE 6

| Swarm no. | LiCl | Mite fall upon LiCl treatment | | | | | | | Sum | Remaining mites | Efficacy (%) |
|---|---|---|---|---|---|---|---|---|---|---|---|
| | | Day 1 | Day 2 | Day 3 | Day 4 | Day 5 | Day 6 | Day 7 | | | |
| 1 | 50 | 1 | 7 | 49 | 89 | 36 | 9 | 16 | 207 | 19 | 92 |
| 2 | mM | 1 | 0 | 8 | 35 | 48 | 7 | 22 | 121 | 23 | 84 |
| 3 | | 0 | 5 | 25 | 87 | 35 | 23 | 32 | 207 | 25 | 89 |
| 4 | 25 | 3 | 6 | 82 | 242 | 108 | 60 | 82 | 583 | 70 | 89 |
| 5 | mM | 7 | 5 | 12 | 165 | 155 | 79 | 163 | 586 | 55 | 91 |
| 6 | | 3 | 3 | 9 | 86 | 183 | 162 | 199 | 645 | 104 | 86 |

The invention claimed is:

1. A method of prophylactic and/or therapeutic treatment of *Varroa destructor* mite infestation of honey bees, the method comprising administering a miticidally effective concentration of lithium chloride salt to the bees.

2. The method of claim 1, wherein the lithium salt is provided as a bee-ingestible composition or sprayable composition.

3. The method of claim 2, wherein the bee-ingestible composition is in liquid form.

4. The method of claim 3, wherein the liquid bee-ingestible composition is a nutritional solution.

5. The method of claim 2, wherein the bee-ingestible composition comprises the lithium salt in a concentration range which is equimolar to the concentration range of about 1 mM to about 150 mM LiCl anhydrous.

6. The method of claim 2, wherein the bee-ingestible composition comprises the lithium salt in a concentration range which is equimolar to the concentration range of about 5 mM to about 100 mM LiCl anhydrous.

7. The method of claim 2, wherein the bee-ingestible composition comprises the lithium salt in a concentration range which is equimolar to the concentration range of about 10 mM to about 75 mM LiCl anhydrous.

8. The method of claim 2, wherein the bee-ingestible composition comprising the lithium salt is administered to the bees.

9. The method of claim 1, wherein the salt of lithium is LiCl anhydrous or hydrated forms thereof.

10. The method of claim 1, wherein the bees are of the genus *Apis*.

11. The method of claim 1, wherein the bees are selected from the group consisting of honeybees, foragers, and hive bees.

12. The method of claim 1, wherein the lithium salt is administered to the bees during a phase of decreased egg-laying.

13. The method of claim 1, wherein the lithium salt is administered to the bees in one or more of September, October, November, and December.

14. The method of claim 4, wherein the nutritional solution comprises ingredients selected from the group consisting of sucrose, corn syrup, sucrose syrup, and mixtures thereof.

15. The method of claim 10, wherein the bees are of the species *Apis mellifera* or *Apis cerana*.

* * * * *